US008458818B2

(12) United States Patent
Neuser et al.

(10) Patent No.: US 8,458,818 B2
(45) Date of Patent: *Jun. 11, 2013

(54) ELASTOMERIC GLOVES AND METHODS OF MAKING

(75) Inventors: Joseph H. Neuser, Green Bay, WI (US);
Larry M. Olson, Kuala Lampur (MY);
Daniel W. Olson, Iron Mountain, MI (US)

(73) Assignee: Sentinal Engineering (M) SDN BHD, Kuala Lumpur (MY)

( * ) Notice: Subject to any disclaimer, the term of this patent is extended or adjusted under 35 U.S.C. 154(b) by 0 days.

This patent is subject to a terminal disclaimer.

(21) Appl. No.: 13/310,738

(22) Filed: Dec. 3, 2011

(65) Prior Publication Data
US 2012/0102620 A1    May 3, 2012

Related U.S. Application Data

(60) Division of application No. 12/774,456, filed on May 5, 2010, now Pat. No. 8,075,965, which is a continuation of application No. 11/463,008, filed on Aug. 8, 2006, now Pat. No. 7,718,240.

(51) Int. Cl.
*A41D 19/02* (2006.01)
(52) U.S. Cl.
USPC .................................. 2/169; 2/168; 427/372.2
(58) Field of Classification Search
USPC .......... 427/372.2, 180; 2/168, 169; 106/162.1
See application file for complete search history.

(56) References Cited

U.S. PATENT DOCUMENTS

| | | |
|---|---|---|
| 3,059,241 A | 10/1962 | O'Brien et al. |
| 3,942,193 A | 3/1976 | Pugh |
| 4,853,978 A | 8/1989 | Stockum |
| 5,014,362 A | 5/1991 | Tillotson et al. |
| 5,133,090 A | 7/1992 | Modak et al. |
| 5,219,340 A | 6/1993 | Seneca |
| 5,534,350 A | 7/1996 | Liou |
| 5,691,287 A | 11/1997 | Villars et al. |
| 5,830,884 A | 11/1998 | Kasica et al. |
| 6,000,061 A | 12/1999 | Taneja et al. |
| 6,004,584 A | 12/1999 | Peterson et al. |
| 6,416,788 B1 | 7/2002 | Barr |
| 6,953,582 B2 | 10/2005 | Chou |
| 2002/0017493 A1 | 2/2002 | Ehrnsperger et al. |
| 2005/0037054 A1 | 2/2005 | Hamann |
| 2005/0076917 A1 | 4/2005 | Wray et al. |
| 2005/0081278 A1 | 4/2005 | Williams |

OTHER PUBLICATIONS

Becker, "Use of Colloidal Oatmeal Inside Rubber Gloves", AMA Archives of Dermatology, 1955:71(), p. 378 (1955).

(Continued)

*Primary Examiner* — Michael C Miggins
(74) *Attorney, Agent, or Firm* — Reinhart Boerner Van Deuren s.c.

(57) ABSTRACT

Elastomeric film-like products such as natural latex gloves are coated with novel lubricity compositions and compositions which protect the skin of the wearer from certain undesirable medical conditions. In powder-coated gloves, the coating composition comprises rice starch, and optionally USP-grade colloidal oatmeal in pharmaceutically accepted concentration. In powder-free gloves, the coating composition comprises colloidal oatmeal enhanced water or beta glucan solution, optionally in combination with one or more other starch components. Colloidal oatmeal enhanced water, and methods of making the colloidal oatmeal enhanced water are also disclosed. In addition, beta glucan solution, and methods of making the beta glucan solution are also disclosed. A liquid referred to herein as Polycoat may also be made by mixing colloidal oatmeal enhanced water with beta glucan solution, and the resulting liquid may be applied to elastomeric articles such as gloves.

15 Claims, 5 Drawing Sheets

OTHER PUBLICATIONS

Sompayrac et al., "Colloidal Oatmeal in Atopic Dermatitis of the Young", Journal of the Florida Medical Association, vol. 45 No. 12 p. 1411-1412, (Jun. 1959).
White et al., "Colloidal Oatmeal as Dusting Powder for Surgical Gloves", Modern Hospital, vol. 93, No. 4, p. 129-130 (Oct. 1959).
Feigenbaum, "Colloidal Oatmeal for Skin Eruptions", Journal of the Medical Society of New Jersey, vol. 54, No. 7, p. 330-331 (Jul. 1957).
Grais, "Role of Colloidal Oatmeal in Dermatologic Treatment of the Aged", A.M.A. Archives of Dermatology and Syphilology, vol. 68 No. 4 p. 402-407 (Oct. 1953).
Yiu et al, Abstract, "Effect of Cooking on Starch and Beta-Glucan of Rolled Oats", Cereal Chem. 64, p. 373-379 (1987).
Hamann, "Review of Natural Rubber Latex Protein Allergy", American Journal of Contact Dermatitis, vol. 4 No. 1, p. 1 and 5 (1993).
"The Only Glove Powdered with Oats", Ostar glove brochure (1997).
Swanson et al, "Latex Allergen Affinity for Starch Powders Applied to Natural Rubber Gloves and Released as an Aerosol: From Dust to Don", Canadian Journal of Allergy and Clinical Immunology, Vol. 5 No. 8, p. 330-336 (2000).
Henry Schein Dental '97 Catalog, p. 158 showing advertisement for Ultravena Ostar latex exam gloves that contain Oat Starch (1997).
Ultravena, "The Natural Solution to Skin Irritation for the Health Care Professional" (1994).

ELASTOMERIC GLOVES AND METHODS OF MAKING

CROSS-REFERENCE TO RELATED APPLICATION

This patent application is a divisional of U.S. Ser. No. 12/774,456 filed on May 5, 2010, which is a continuation of U.S. Ser. No. 11/463,008 filed on Aug. 8, 2006. Both of these parent application are incorporated herein by reference.

BACKGROUND

1. Technical Field

This disclosure generally relates to methods for making elastomeric gloves, and more specifically relates to methods for making elastomeric gloves that include one or more coatings derived from oats.

2. Background Art

As is known in the art, flexible impermeable elastomer-based gloves include both disposable gloves and reusable gloves. The aforementioned gloves (as well as certain other flexible elastomeric articles which are used adjacent the skin or other membrane of a user's body) are thin, flexible, and fluid impermeable. The substrate body of the glove can generally be formed from any of a wide variety of natural rubbers and/or synthetic elastomeric materials known in the art. For instance, some examples, without limitation, of suitable materials useful in making the glove substrate body include, but are not limited to, certain materials characterized as SEBS (styrene-ethylene-butylene-styrene) block copolymers, SI (styrene-isoprene) block copolymers, SIS (styrene-isoprene-styrene) block copolymers, SBS (styrene-butadiene-styrene) block copolymers, SB (styrene-butadiene) block copolymers, natural rubber latex, nitrile rubbers, isoprene rubbers, chloroprene rubbers, polyvinyl chlorides, silicone rubbers, elastomeric polyurethanes, neoprene, butadiene methylmethacrylates, acrylonitriles, acrylate-based hydrogels, and combinations thereof. Other suitable elastomeric materials can also be used to form the substrate body of the glove. Those skilled in the art are well aware of the various materials from which such gloves can be made.

The glove substrate body is generally considered to be that structure which provides the primary structural strength to the glove. The glove substrate can be fabricated with a single layer of substrate material, or multiple layers of substrate material. In gloves which have multiple substrate layers, all the layers can be defined by a common substrate material composition, or one or more of the layers can be defined by second and optionally additional different substrate material compositions.

In fabricating a glove, typically, the elastomer composition from which gloves are to be formed is expressed in a liquid form. For example, the elastomer can be suspended in an emulsion. Glove molds, for example ceramic molds, are dipped into the emulsion, thereby coating material from the emulsion onto the molds. The molds can be removed from the emulsion, the liquid carrier can be flashed off from the molds, and the latex can be cured and/or vulcanized or otherwise treated, thereby to leave the glove substrate material coated onto the respective molds. The glove substrates can be coated with a donning agent, then stripped from the molds and inverted. The glove substrates are typically inverted in the process of being stripped from the molds. In the alternative, the glove substrates can be first stripped from the mold without having been coated with a donning agent, and subsequently coated with any desired donning agent.

A typical glove has a non-wearer-contacting surface, generally referred to as an "outer surface", or an "outside surface". The glove also has an opposite, wearer-contacting surface.

The materials commonly used to form glove substrates and substrate layers, for example natural latex rubber, tend to be sticky or tacky, which makes it difficult to don the glove, namely to put the glove on the user's hand. The commonly-used substrate materials also tend to trap perspiration from the user's hand inside the glove.

Disposable gloves are widely used by members of the medical community, the scientific community, and the industrial community to protect the wearer from chemical exposure, mechanical abrasion, environmental hazards, and biohazard contamination, and to prevent transmission of disease or contaminants. Health care providers commonly wear gloves for a single use while performing surgery or other medical or dental procedures such as patient examinations. Thus, the gloves which are the subject of this disclosure are often referred to as disposable examination gloves or disposable surgical gloves, and in general as disposable gloves.

The glove substrates of gloves discussed herein are designed to be generally impermeable to biological fluids, tissues, and solids which are produced by the body, as well as being generally impermeable to other contaminants (human or animal), thus advantageously protecting the wearer from fomitic transmission (transmission by objects that harbor pathogenic organisms) of pathogens and diseases.

Gloves are also worn by individuals who wish to protect their hands from various chemicals, materials, and objects which may irritate, damage, dry out, or otherwise negatively affect the user's skin, and which may be harmful or potentially harmful if allowed to contact or permeate the dermal barrier. Scientists, cleaning service workers, food processing workers, food handlers, law enforcement workers, beauticians or other workers having special protection needs, wear such gloves in the occupational environment. Thus, gloves discussed herein can also include protective gloves or industrial gloves. Also, some gloves, for example household gloves or gardening gloves, are made with more durable substrates, for example thicker substrates, whereby the gloves are considered reusable gloves because they can be used multiple times prior to disposal, and the anticipated uses carry lower risk of deleteriously contaminating the user from outside sources, or of deleteriously contaminating a person being serviced by the user.

In a medical or other intimate use environment, flexible elastomer articles, such as disposable gloves, are frequently changed by the wearer during the day between patients or between procedures or other activities. Allergy and irritation potential of a finished disposable glove has been exacerbated by common glove manufacturing practices of using vulcanizing accelerators, antioxidants, certain powders and other additives as a means to speed production of the glove substrate, to ease donning of the glove, to prevent or cover tackiness, to enhance durability during storage and use life of the glove, and the like. In addition, when conventional disposable gloves cover the hand, moisture (perspiration) is trapped between the skin of the hand and the inner surface of the glove, contributing to hand dermatitis, and potentially other skin problems. Some healthcare providers assertedly struggle with allergic or irritant contact dermatitis or IgE mediated latex hypersensitivity (Type I) whereby such individuals carry an artificially heightened susceptibility to skin disease or infection.

In attempting to address such skin-care issues, some glove users apply lotions, creams, and/or other emollients in attempts to moisturize their hands. Such emollients frequently are oil-based which can deleteriously affect a natural latex rubber glove. Further, such emollients sometimes contain certain antigenic chemicals which serve to exacerbate the above-mentioned and/or other skin problems.

The art has responded to the tackiness and donning problems of elastomer-substrate gloves in a number of ways. One solution which has been suggested for addressing the aforementioned donning problems is to treat the glove with a powder, such as cornstarch, oat starch, talcum (talc) powder, other starch dusting powders, polyglycolic acid powder, insoluble sodium metaphosphate powder, magnesium carbonate, or granular vinyl chloride polymer. Some such powders are used in combination with other powders or with other ingredients. Most elastomers from which the glove substrate is made are inherently sticky on their surfaces, causing a blocking effect, which makes it difficult to don the glove, put the glove on, without the assistance of a donning agent. Commonly, a cross-linked cornstarch powder is used inside the glove, as a donning agent, to facilitate donning the glove.

The aforementioned powders can provide apparent comfort to the wearer's hand as the hand moisture builds up within the glove as the glove is used, but conversely can also act to dry, to abrade and/or to otherwise irritate the user's skin.

The substrate materials most commonly used in fabricating glove substrates which are used to make gloves are natural latex rubbers. It is known that natural latex rubber antigenic proteins migrate to the surface of a disposable natural latex rubber glove substrate, or other flexible article, and are known to have a propensity to electrochemically bind to the cross-linked cornstarch powder particles which are typically used as a donning coating on such natural latex rubber gloves.

The cornstarch particles serve as vehicles to carry the antigen proteins. Such carrying of the proteins has been shown to be problematic to a fraction of the users of such gloves, in that a certain amount of the powder may be aerosolized from the glove during normal use and disposal of the glove. Such aerosolized powder particles can be inhaled by the wearer of the glove, or other person in the vicinity, during normal breathing, whence such powder is delivered to the immunoactive tissue of the nasopharynx and the bronchial tree, where the respective proteins may be harmful. This delivery and corresponding bodily response mechanism occurs because macrophages and specialized T cells and B cells which are concentrated in the tissue of the nasopharynx and bronchial tree become sensitized and produce IgE specific antibodies, which recognize the natural latex rubber antigens, carried by the cornstarch. Thus, cornstarch powder used in natural latex rubber gloves can cause systemic natural latex rubber allergies and skin irritation, and can exacerbate contact allergies.

Another problem with the use of certain powders, such as talc and cornstarch, in surgical gloves is the concern about adhesion formation in a patient's surgical site. This is a particularly significant problem as an intraperitoneal postoperative complication where adhesions of the bowel cause significant sequellae in some patients. As a partial response to this issue, surgeons are provided with towels after donning surgical gloves, for use to wipe off as much of the powder as possible. However, such procedure is not completely successful whereby a certain amount of powder remains on the gloves after such wiping action. The remaining powder particles are known to be responsible for irritation which allegedly can produce scarring in the surgical site, which scarring can be responsible for development of adhesions. The adhesions are caused by mechanical irritation of the tissue when the powder particles are sequestered in the surgical site.

Such complications in the surgical site have been instrumental in the development of glove coating alternatives for gloves which are used for surgical procedures. Such alternatives replace gloves which are coated with powdered talc or corn starch, with powder free gloves which are coated with a powder-free coating.

Balanced against the disadvantages of using surface powders such as talc, cornstarch, and oat starch, is the advantage that surface powders assist in mitigating the inherent tackiness of most elastomers, as well as in facilitating donning the gloves. In order to detackify the non-wearer-contacting surface of the elastomer glove, a detackifying agent needs to be applied to that surface as well. A detackifying agent can be applied to the non-wearer-contacting surface as part of normal processing of a glove disposed on a glove former, to which powder is applied at the wearer-contacting surface. Such gloves can be stripped from the substrate-forming mold after being coated with powder, and can be subsequently processed in a tumbler in order to more evenly distribute the powder and/or to remove any excess powder. During such tumbling, some of the powder is dislodged from the inner surface of the glove, and contributes to the powdering of the outer surface of the glove. Thus, by the time the glove has passed through the tumbling process, powder is present on both the wearer-contacting surface of the glove and on the wearer non-contacting surface of the glove. Typically, and desirably, there is more powder on the inner surface of the glove than on the outer surface of the glove. The powder on the inner surface of the glove prevents the glove from sticking to itself and aids in the donning of the glove. The powder on the outer surface of the glove prevents adjacent gloves, e.g., in a box of gloves, from sticking to each other. Thus, the surface powders, when acting as detackifiers, reduce the tendency of a glove to stick to itself such as on the inside of the glove, and to stick to other gloves when a plurality of gloves are tightly packed together in glove dispensers, or boxes of gloves. Thus, it is seen that the surface powder coatings act as detackifiers to prevent the surfaces of the gloves from sticking to each other, either within a given glove, or glove-to-glove. In addition, the surface powder coatings act to facilitate donning of the gloves.

Use of a powdered donning lubricant such as talc, cornstarch, or oat starch is preferred by some glove users, over lubricant coatings applied to the wearer-contacting surface of the glove or to powder free gloves, in some respects because powder-based donning lubricants are effective to reduce frictional forces which must be overcome when the glove is put on/donned by the user.

Some fabricators of gloves have used halogenation, such as chlorination, and neutralization to solve the tackiness and donning issues of gloves which employ elastomer-based substrates. Other fabricators of gloves which employ elastomer-based substrates have used other surface treatments such as powder free glove coatings using alternative lubricants, for example silicone treated gloves, polyurethane treated gloves, gloves treated with a polymer coating such as an acrylic coating, to solve the aforementioned problems with tackiness, as well as to address the issues attending powder-coated gloves in surgical uses. Such surface treatments typically include coatings applied to the wearer-contacting surface of the glove.

A coating is a material which provides an additional functionally effective layer, whether continuous or discontinuous, on the surface of the glove. Where the coating is discontinuous, generally the coating is provided by a powder which is resident on the inner surface of the glove as well as being optionally resident on the outer surface of the glove. The quantity of the powder, or rate of addition per unit area of the glove, is typically higher on the inner surface of the glove than on the outer surface of the glove.

Where the coating is continuous, the coating is typically defined as a continuous film which has been deposited on at least one of the inner surface and the outer surface. In a film-type coating, the rate of addition per unit area is typically directly related to the thickness of the coating whereby the relative quantity of coating material on the inner surface and the outer surface can be related to the relative thicknesses of the coatings on the respective surfaces. Similarly, the uniformity of the coating can be determined by measuring the thickness of the coating at various locations on a given surface.

In light of the issues related to skin problems with elastomeric gloves, there exists a demand for gloves which have improved coatings, both powder coatings and non-powder coatings.

There further exists a demand for coatings which use less coating material while achieving the combined objectives of ease of donning the glove and reducing the cost of the coating.

There also exists a demand for coatings which are less costly to produce per unit mass, and which can be employed in less mass per glove.

There still further exists demand for coatings which can be produced in the same geographical regions where high volumes of glove substrates are being produced.

There exists yet additional demand for gloves which provide pleasant tactile feel to the wearer of the glove.

There exists yet further demand for coatings which address and ameliorate skin problems which purportedly can attend use of such gloves.

There exists a yet further demand for coatings which address and ameliorate the skin problems which commonly attend use of such gloves by incorporating in the coatings material which is pharmaceutically effective as a skin protectant in treating the types of skin problems which are commonly developed by people who use such gloves for substantial portions of their work days.

BRIEF SUMMARY

The gloves disclosed herein meet many of the demands listed above. It is not required that any one embodiment meet all of the above demands. While certain embodiments exhibit improvements in several of the above demand features, this disclosure and claims herein extend to any embodiment that achieves improvement in at least one of the above demand features.

To that end, a first embodiment of gloves includes a polymeric glove substrate according to conventional technology, which is generally impermeable to biological fluids, tissues, and solids which are produced by the body. The glove substrate can employ a single layer of substrate material, or multiple layers of substrate material. Where multiple layers of substrate material are used, the substrate layers may all have substantially the same composition, or can employ different compositions. The glove substrate is coated on the inner, wearer-contact surface, with a powder coating. The powder coating is defined largely by powdered rice starch. The rice starch particle size is quite small, such as about 2 to 8 microns, whereby the tactile feel of the coated glove is quite pleasant to the skin. The particle size of rice starch is about three times smaller in average size in comparison to cornstarch so there is a significant improvement in the tactile feel of the glove.

In a second and related embodiment of powder coated gloves, colloidal oatmeal powder is added to the rice starch. The colloidal oatmeal powder used is optionally a United States Pharmacopoeia (USP) grade colloidal oatmeal powder, and is optionally used in the coating composition in a quantity which makes a pharmaceutically effective skin-protectant presentation to the skin, whereby the pharmaceutical benefits of the colloidal oatmeal powder can be achieved. By giving colloidal oatmeal a USP designation, the United States Food and Drug Administration has recognized that colloidal oatmeal is an over-the-counter drug that heals and protects the skin.

In a third and also related embodiment, the colloidal oatmeal powder is incorporated into a water-based carrier liquid. Supernatant portions of the resulting liquid composition can be referred to as "colloidal oatmeal enhanced water" (COEW). COEW can be employed as a coating on a variety of products which have elastomeric substrates, or other polymeric substrates, and especially products which effectively come into contact with a user's skin or other sensitive body tissues for prolonged periods of time. Various methods/processes can be used to apply a coating of COEW onto a polymeric substrate. The substrate can be dipped into a bath of the COEW, passed under a cascade of the COEW, or the substrate can receive a spray application of the COEW. The COEW can be incorporated into a mold release liquid bath. The gloves can be tumbled in a tumbler in the presence of COEW. Where the substrate is available in a sheet-like form, the coating can be applied by any of the methods which are generally known for coating sheet stock such as in the paper coating industry or the plastic film industry. Those skilled in the art are aware of various other methods of applying a liquid coating to a polymeric substrate. The substrate can also be pre-treated, such as with various primer materials, or can be irradiated or corona treated to enhance adhesion of the COEW if and as desired.

In a fourth and also related embodiment, the COEW is coated onto an elastomeric glove substrate, especially onto that surface of the glove substrate which will form the inner surface, the wearer-contact surface, of the glove. The combination of the mass per unit of area of the coating, and the concentration of the colloidal oatmeal in the COEW, are sufficiently great that the quantity of colloidal oatmeal which is presented to the skin is effective to protect from, to treat for, and/or to attenuate, the various skin issues which can attend such extended-time use of such gloves.

In a fifth and also related embodiment, a beta glucan solution (BGS) is used to coat an elastomeric glove substrate, especially onto that surface of the glove substrate which will form the inner surface, the wearer-contact surface, of the glove. The combination of the mass per unit of area of the coating, and the concentration of the beta glucan in the coating, are sufficiently great that the quantity of beta glucan which is presented to the skin is effective to protect from, to treat for, and/or to attenuate, the various skin issues which can attend such extended-time use of such gloves. In addition, the beta glucan gives the gloves a silky feel when donning and provides a residue on the hands of the user that provides a silky feel on the user's skin even after the gloves are removed from the user's hands. Oat beta glucan is one specific example of a suitable beta glucan that may be used to manufacture BGS.

In a sixth and also related embodiment, COEW and BGS are mixed to form a liquid referred to herein as Polycoat. Polycoat may be coated onto an elastomeric glove substrate, especially onto that surface of the glove substrate which will form the inner surface, the wearer-contact surface, of the glove. The combination of the mass per unit of area of the coating, and the concentration of the colloidal oatmeal and beta glucan in the Polycoat coating, are sufficiently great that the quantity of colloidal oatmeal and/or beta glucan which is presented to the skin is effective to protect from, to treat for, and/or to attenuate, the various skin issues which can attend such extended-time use of such gloves. The inclusion of Colloidal Oatmeal USP in Polycoat provides medical benefits to the skin of the user of the glove. In addition, the beta glucan in the Polycoat gives the gloves a silky feel when donning and provides a residue on the hands of the user that provides a silky feel on the user's skin even after the gloves are removed from the user's hands.

The size of particulates in the liquid coatings that include COEW, BGS, or both (Polycoat) is preferably controlled to be less than a predetermined maximum particle size. As a result, a coating that uses these materials results in a fine powder that aids in donning the glove, but the powder is not detectable using the standard ASTM D6124 test, resulting in a glove that may be easily donned due to the fine powder coating but still qualifies as a powder-free glove under industry standards.

The foregoing and other features and advantages will be apparent from the following more particular description, as illustrated in the accompanying drawings.

BRIEF DESCRIPTION OF THE SEVERAL VIEWS OF THE DRAWING(S)

The disclosure will be described in conjunction with the appended drawings, where like designations denote like elements, and:

Figure 1:
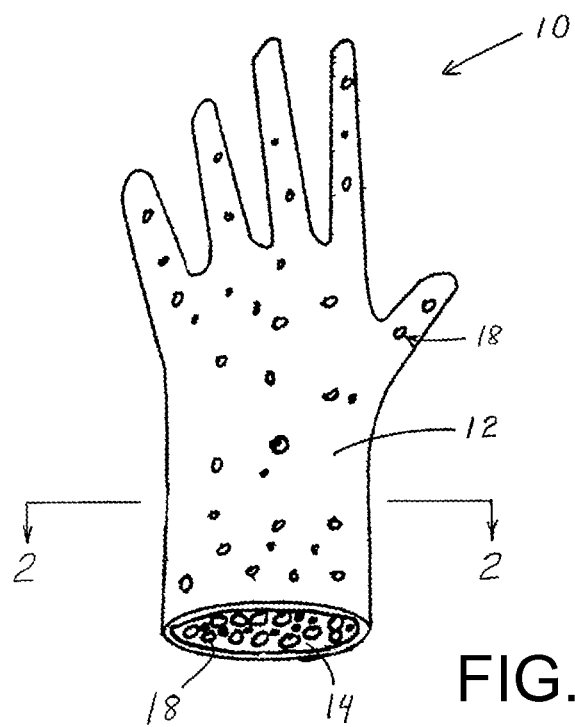
FIG. 1 shows a perspective view of one embodiment of a powder-coated elastomeric glove.

The disclosure and claims herein are not limited to the details of construction or the arrangement of the components set forth in the following description or illustrated in the drawings. The disclosure and claims are capable of other embodiments or of being practiced or carried out in other various ways. Also, it is to be understood that the terminology and phraseology employed herein is for purpose of description and illustration and should not be regarded as limiting.

DETAILED DESCRIPTION

The botanical sources of rice starch are generally defined by the genus oryza, typically from the species sativa, alternatively the species glaberrima. However other species are known, and are included in the definition of rice herein. As used herein, the term "rice starch" includes the named species rice and other species of the rice plant, as is known in the art. The preferred dry powdered rice starch is rice starch powder commercially available as a freeze-dried powder or a dehydrated powder. Rice starch is readily available from a wide variety of commercial sources. The sizes of rice starch powder particles cover a substantial size range, with average particle size generally in the range of about 2 microns to about 8 microns.

Figure 2:
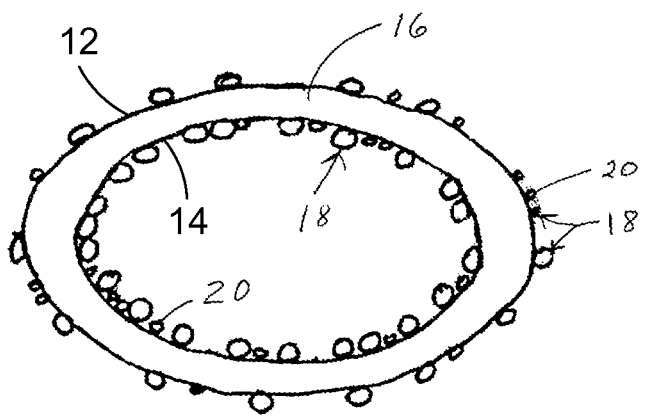
FIG. 2 shows a cross-section of the glove of FIG. 2.

Referring now to FIGS. 1 and 2, a flexible impermeable elastomeric glove is designated generally as 10. As shown in FIGS. 1 and 2, glove 10 has an outer surface (non-wearer-contacting surface) 12 and an inner or wearer-contacting surface 14 and the elastomeric glove substrate 16 therebetween. Substrate 16 can include one or more layers of elastomer or blended elastomers. As best shown in FIG. 2, wearer-contacting surface 14 has a dry powdered material 18 applied thereto. Dry powdered material 18 is typically dry powdered rice starch, or predominantly dry powdered rice starch. The particles in FIGS. 1 and 2 are not drawn to scale. Glove 10 is made generally as follows. A dry flexible glove substrate is oriented with the dry wearer-contacting surface facing outwardly, such as on a glove mold. Dry powdered material 18 is applied to the dry but tacky flexible elastomeric glove substrate at the then-outwardly-facing wearer-contacting surface. The glove is inverted so the wearer-contacting surface is facing inwardly in the resulting glove. Dry powdered material 18 is applied while the wearer-contacting surface is facing outwardly using any suitable application method, including without limitation aerosol application, electrostatic deposition, tumbling, use of a powder bed, either fluidized bed or non-fluidized bed. Other methods of applying dry powdered material 18 will be known to those skilled in the art.

The percentage concentration of dry powdered material 18 on the surface of glove 10 ranges from about 0.0005 percent by weight to about 3.0 percent by weight of dry powdered material, based on the weight of substrate material 16. In some embodiments, dry powdered material 18 is about 0.02 percent by weight to about 1.5 percent by weight based on the weight of the substrate material, with the most preferred being 1.35 percent by weight. The coating weight range percentage can be adjusted depending on the type of glove made and proprietary process nuances. Certain gloves may require up to about 25 percent by weight or greater of dry powdered material 18 based on the weight of the glove substrate.

For a batch of 8,000 to 10,000 medical examination gloves preferably about 1 kilogram of dry powdered material 18 is used. The percentage for the dry powdered material 18 can also be determined by industry standards or guidelines, such as by ASTM Standard D6124 (ASTM International, West Conshohocken, Pa. 19428-2959, United States) for gloves. Dry powdered material 18 serves as a moisture regulator, as a lubricant, and as a donning agent and, depending on the composition of material 18, may impart a range of therapeutic benefits and comfort to the wearer. The therapeutic benefits of rice starch are discussed in a 2002 article by Darin Engles which was published as a Healthnotes Newswire on the website for the Bastyr Center for Natural Health.

One advantage of the dry powdered material used to coat gloves is that dry powdered material 18, when applied to the glove substrate, provides even greater apparent lubricity characteristics than known powder coating materials such as cross-linked corn starch due to the smaller particle size.

A further advantage is that the rice starch particles do not bind to latex proteins from natural rubber latex as readily as cross-linked cornstarch. Another advantage is that rice starch is not cross-linked, thereby reducing the number of steps necessary in the production of the powdered coating material. In addition, the therapeutically important molecules in dry powdered material 18 are not deactivated by a heating step. Thus, the full potency of the therapeutically important molecules of dry powdered material 18 are available from glove 10. In the global economy, such therapeutic potency can define a competitive edge in the market. Substrate 16 of glove 10, having the dry powdered material 18 applied thereon, can be either a single layer substrate, or a multiple-layer substrate. In a multiple-layer substrate, all of the layers can have a common composition, or one or more of the layers can have compositions which are different from the compositions of one or more other ones of the layers. The specific layer compositions for glove substrate 16 can be well selected by those skilled in the art who are familiar with substrate compositions and methods for fabricating such substrates for a specific glove application.

Dry powdered material 18 (which includes substantially dry powdered rice starch) may permissively, but not necessarily, be fortified with colloidal oatmeal. Colloidal oatmeal is a commercially available product well known in the art, and generally is represented by the product resulting from comminuting whole grains of oats to a desired average particle size of 4 microns to about 30 microns. Colloidal oatmeal is typically added in an amount of at least 0.003 percent by weight, optionally at least about 10.0 percent by weight, based on the total weight of the powder coating material.

In addition, or in the alternative, powdered material 18 can be further fortified with one or more commercially available additives, in addition to the optional addition of colloidal oatmeal, which are known to protect and restore mammalian tissue such as skin or other membranes. Suitable additives 20 which may be included in powdered material 18 include, without limitation, any one or more of Vitamin A, Vitamin B3, Vitamin B5, Vitamin C, Vitamin E, jojoba, rose hips, aloe vera, dried tea tree oil, dried flax seed oil, dried palm oil, and acetylsalicylic acid. Such additives may be added in amounts to meet content labeling requirements known in the industry.

Optionally, the dry powder material coating contains rice starch, preferably as a predominant component, and may include colloidal oatmeal as well as any, or any combination, of the known additives which are known to protect and/or restore mammalian tissue. The most preferred additive ingredient is colloidal oatmeal, with secondary preference for Vitamin E. In some implementations, the powdered rice starch can function as a delivery agent for additive 20, maximizing the bioavailability of additive 20, as well as optionally contributing, itself, to the protection and/or restoration of the tissue being treated.

Hand sweating beneath a glove, with extensive use of such gloves, is known to be a contributor to irritant contact dermatitis. Advantageously, rice starch provides better water absorption properties, compared to cornstarch, silicone and polyurethane which are commonly used as donning agents. The ability to absorb the perspiration without abrasive properties, while reducing the cost of the powder coating material, is an advantage over known art. The cost per weight unit of the powder coating 18 is typically more than cross-linked cornstarch, but less powder coating 18 is required than the cross-linked cornstarch, resulting in a net reduction in the cost of powder on a glove. The improvement of therapeutically protecting the skin is a function of the ability of dry powder 18 to overcome water homeostasis after glove 10 is donned by a wearer.

As can be appreciated by those skilled in the art, other dry powdered materials can be used in combination with dry powdered rice starch and/or dry powdered colloidal oatmeal. These materials can include, for example and without limitation, one or more dry powdered plant materials such as okra, kelp, tamarind, psyllium, carrageenan, chia, flax, carob, guar, xanthan, konjac, cassia, tara, karaya, ghatti, tragacanth, glucomannan, or galactomannan. Such dry powdered materials are commercially available, for example, from NHK Laboratories, Inc., 12230 E. Florence Ave., Santa Fe Springs, Calif. 90670-3806 (866) 645-5227; Aloe Laboratories, 5821 East Harrison, Harlingen, Tex. 78550 (956) 428-8416; Voigt Global Distribution LLC, P.O. Box 412762, Kansas City, Mo. 64141-2762 (877) 484-3552; Natunola Health, 661 St. Lawrence Street, Winchester, Ontario, Canada K0C 2K0 (613) 774-9998; P. L. Thomas, 119 Headquarters Plaza, Morristown, N.J. 07960 (973) 984-0900; Kingreat Chemistry Co., Ltd., Jinyuan Plaza 57, Hubin Road(S), XIAMEN, Fujian, China 361004 86-592-2299-609; Konjac Foods, 355 W. Olive Ave., Suite 104, Sunnyvale, Calif. 94086 (408) 257-1813; Glucomannan.com, 20432 Silverado Ave., #212, Cupertino, Calif. 95014; Cognis UK Ltd., Charleston Road, Hardley, Hythe, Southampton, Hampshire, SO45 3ZG United Kingdom.

In a method of making flexible elastomer glove 10, a cleaned ceramic glove mold is passed into a dip tank containing mold release agent. The so-coated mold is then passed through an oven to bring the mold to the desired coating temperature. The mold is then dipped in, passed through, an open-topped tank of liquid which contains latex which is to be used to form a glove substrate on the mold. The so-coated mold is passed through an oven to accomplish pre-vulcanization of the latex rubber which has been coated onto the hand-shaped mold. The mold, with the latex coating thereon, is then contacted with a leaching agent, for example in another open top tank, to wash off excess uncured latex and residual monomer, as well as to reduce protein content of the latex. The glove substrate so formed, still on the mold, is then passed through a tank which applies powder 18, as a water slurry coating, to the outer surface of the tacky latex substrate. The coated glove is then passed through another drying oven, which further cures the latex as well as driving off the water carrier from the powder-coating slurry.

The so-coated glove is then stripped from the mold, and is inverted in the stripping process, such that the previously-outside surface of the glove on the mold becomes the inner surface of the inverted glove. The glove can then be put in a tumbler/dryer for final drying and vulcanization. During the tumbling action, some of the powder, now on the inner surface of the glove, becomes dislodged, moves outside the inside enclosed area of the glove and becomes lodged on the outer, non-wearer contacting, surface of the glove, thereby to lubricate such outer surface.

The dry flexible elastomeric glove substrate, made according to the above glove manufacturing process, is oriented such that the dry wearer-contacting surface is disposed/directed outwardly, so as efficaciously to receive dry powdered material 18 as such dry powdered material 18 is applied to the wearer-contacting surface. Dry powdered material 18, such as dry powdered rice starch with or without the aforementioned colloidal oatmeal or additives 20 or plant materials, is typically applied to the dry wearer-contacting surface of the dry flexible elastomer glove.

Starting with the glove on the ceramic glove mold, glove 10 is ultimately inverted such that the outer surface, namely the non-wearer-contacting surface 12, is facing outwardly relative to the glove, and the wearer contacting surface 14 is directed inwardly into the glove as shown in FIG. 1. After the glove is thus coated, and after the glove is inverted as the glove is being removed from the mold, glove 10 is further processed according to known-in-the-art glove finishing processes which do not require the addition of moisture and which optionally do not require application of heat to the glove.

Any flexible elastomer article can be produced according to the same method. For example, a dry elastomer article is made according to known techniques and is oriented with the wearer surface facing outwardly away from the article. Dry powdered material 18, such as dry powdered rice starch and optionally dry powdered colloidal oatmeal, with or without any additives 20, is applied to the dry wearer-contacting surface of the dry elastomer article. The article is inverted and may undergo further tumbling and/or other processing as described for gloves and/or as is typical for such articles.

The amount of the dry powdered material used is in a quantity sufficient to meet industry standards or guidelines, such as, but not limited to, the International Starch Institute criteria for residual rice starch in the article, the aforementioned ASTM standards, as well as publicly-known glove industry standards. The quantity of dry powdered rice starch material ranges from about 0.0005 percent by weight to about 3.0 percent by weight of dry powdered rice starch material, preferably about 0.02 percent by weight to about 1.5 percent by weight dry powdered rice starch material 18, based on the weight of the substrate material.

An exemplary method of applying the dry powdered rice starch material to a dry wearer-contacting surface of a dry flexible elastomer glove includes selecting a dry flexible elastomer glove oriented to receive a material to be applied to a dry wearer-contacting surface of the glove. The glove is optionally still on the ceramic substrate former mold. The dry powdered material 18, with or without colloidal oatmeal or additives 20, is applied to the outwardly-facing dry wearer-contacting surface of the glove by any suitable method, including without limitation aerosol application, electrostatic precipitation, tumbling, passing the glove substrate through a bed, either fluidized or non-fluidized, of the dry powdered material, or dipping the glove substrate in a tank of liquid which contains the coating powder in a slurry.

In a specific exemplary method, dry powdered material 18 is aerosolized using pressurized nozzles disposed in a negative pressure chamber through which the dry gloves pass, still on the substrate formers. The dry powdered material adheres to the surface of the elastomer (polymer) material of the glove because of the inherent tackiness of the elastomer material. The dry powdered material is in a fine cloud form having a particle size typically about 8 microns or less, more typically about 6 microns or less. In general, the smaller the particle sizes result in greater wearer perception of improved lubricity in donning the glove 10. In addition, smaller particle size typically means that relatively less dry material is used, compared to a powder which employs larger-size particles.

The quantity of dry powdered material 18 deposited is generally proportional to the aerosolized concentration of dry powdered material in the negative pressure chamber and the length of time in the chamber. Typically, about 2 kilograms of the dry powdered material is used for 8,000-10,000 gloves. After the gloves are so powder-coated, the gloves are removed from the powder-coating chamber and each glove is inverted as it is pulled from the former, such that the resulting powder-coated gloves are oriented with the coated surface on the inside of the glove. It will be understood that a lesser weight portion of the coating is also resident on the now outwardly-facing surface of the glove.

In another exemplary method, the dry powdered rice starch material can be electrostatically applied to a dry wearer-contacting surface of a dry glove. A completely dry glove is disposed on a glove former. An electrostatic charge is applied to the glove former whereby there is a difference in charge between the former and the glove surface. The electrostatic charge creates a static charge difference between the wearer-contacting surface of the glove and dry powdered material 18. The dry powdered material, with or without the colloidal oatmeal or additives 20, is applied in aerosol form, as an aerosolized dry powder, to the glove while the glove is on the former. The charge difference attracts the aerosolized powder to the wearer-contacting surface of the glove. The electrostatic deposition process holds potential for less waste of the dry powdered material in the powder deposition step, thereby reducing cost of material. Since the powder is better controlled by the electrostatic process than in the reduced pressure process, the electrostatic process, including dust control, can be easier to manage in the manufacturing setting. Alternatively, rather than applying an aerosol form of the dry powdered material 18, with or without the colloidal oatmeal or additives 20, the glove is sprayed or dusted with the dry powdered material until the dry wearer-contacting surface of the glove is covered with the dry powdered powder. Again, each glove is inverted as it is pulled from the former, after being coated with the powder.

Figure 3:
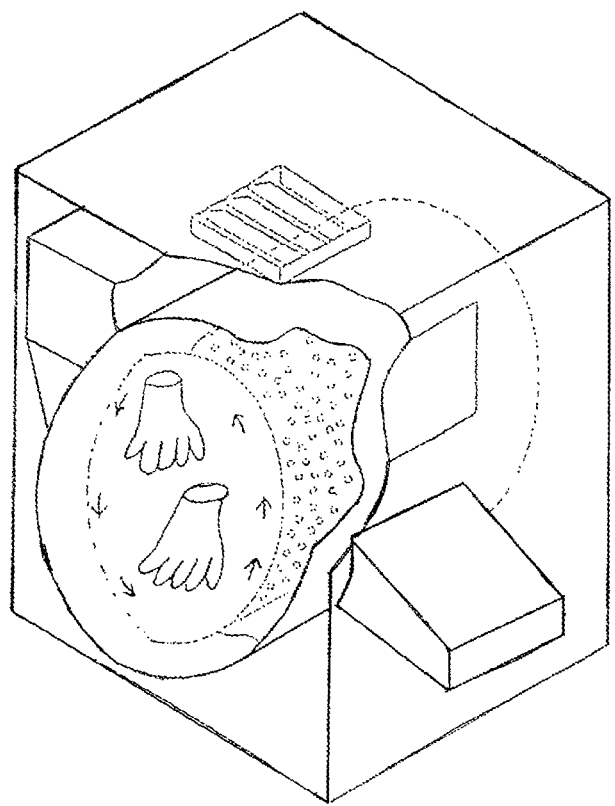
FIG. 3 shows one method of applying the powder coating to gloves.

In yet another different process, dry powdered material 18 is applied to the dry glove by tumbling the dry powdered material 18 with the dry glove in a tumbling chamber of a glove tumbler, as shown in FIG. 3. As is known in the art, in some glove making processes, a glove is dried in a glove tumbler with the dry glove oriented in such a manner that the dry wearer-contacting surface is facing outwardly. The dry powdered rice starch material, with or without colloidal oatmeal or the dry additives, is added to the glove tumbler. Dry powdered material 18 can be in an aerosol form as disclosed above, or in a non-aerosol form when added to the tumbling chamber. The gloves are tumbled until the dry powdered rice starch material covers the gloves, for approximately 2-5 minutes for 8,000 to 10,000 gloves, using approximately 2 kilograms of the dry powdered material.

During the tumbling operation, the dry wearer-contacting surface of each glove is facing outwardly and is put into the glove tumbler with the dry powdered rice starch material and tumbled without applied heat until the dry powdered material generally uniformly covers the dry wearer-contacting surfaces 14 of the gloves 10. The gloves are inverted after tumbling so that the coated non-wearer-contacting surface 12 is disposed outwardly as shown in FIG. 1. In tumbling processes, as well as in the aerosolized processes, some of the dry powdered material adheres, as well, to the non-wearer contacting surface 12.

Still yet alternatively, in a glove stripping station, a bed of the dry powdered material 18, with or without additives 20, is disposed along the production line. The bed of dry powdered material 18 can be non-fluidized or fluidized. A fluidized bed means that the dry powdered material is aerated so as to facilitate passage of a material or article through the bed. Namely, air is caused to bubble up through the dry powdered material. The gloves pass through the bed of dry powdered material 18 whereby the gloves are coated with the powder. Each glove is inverted, as usual, as the glove is removed from the mold. The amounts of the dry powdered material 18 which are coated onto the gloves are as described above.

The mean and median particle size of the un-crosslinked native rice starch powder used in powdered material 18 is smaller than the mean and median particle size of the cross-linked powdered corn starch used in the prior art. This smaller particle size results in a number of benefits. First, since the uncross-linked rice starch particles are smaller, the typical amount of rice starch powder material which is used is less than the amount of cross-linked corn starch material which would be used on the same glove. Second, uncross-linked rice starch is readily available in Asia where many latex glove substrates are made. Third, since the particle size of the rice starch is relatively smaller, the feel of the glove is that of a relatively smoother, finer-textured coated surface of the glove. Fourth, where USP-grade colloidal oatmeal is used in combination with the rice starch, the USP pharmaceutical benefits of the colloidal oatmeal further address protection of the user's skin from skin problems such as those discussed above.

Figure 4:
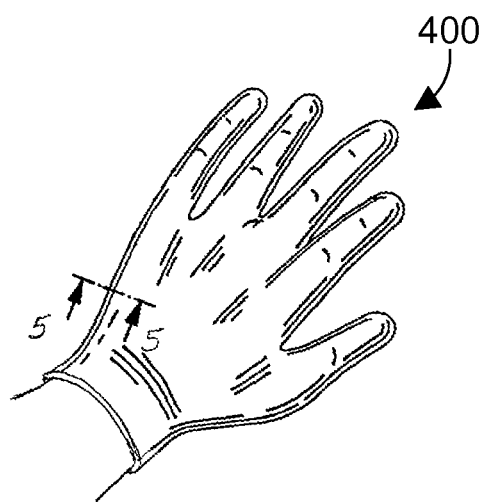
FIG. 4 shows a perspective view of one embodiment of a non-powder coated glove.
Figure 5:
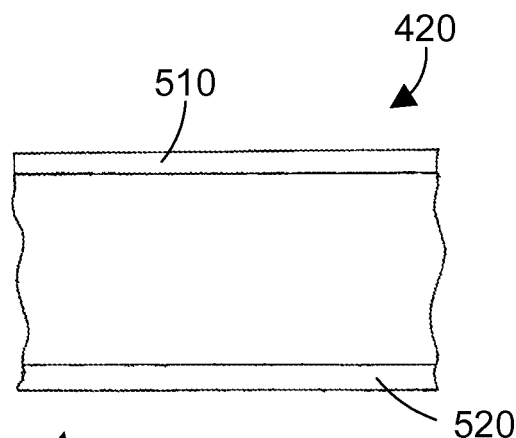
FIG. 5 shows a cross-section of the glove of FIG. 4, taken along the line 4-4.

FIGS. 4 and 5 illustrate a powder free glove 400. Glove 400 includes an inner cavity that defines an inner surface 440 that contacts the wearer's hand and an outer surface 420, as shown in FIG. 5. Either or both of surfaces 420 and 440 may include a dry coating, shown in FIG. 5 as a layer 510 on the outer surface 420 and a layer 520 on the inner surface 440. Note that layer 510 on outer surface 420 is optional for some glove applications, but many manufacturing methods for applying coating layer 520 to the inner surface 440 may also produce a residual coating layer 510 on the outer surface 420 as well. As used herein, "powder free" means that the gloves, on average, have less than 2 milligrams of particulate, when tested according to ASTM D6124.

In a powder free glove, the publicly recognized purpose of the glove coating is to facilitate donning of the glove by a lubricity functionality. Synthetic polymer based coatings, such as acrylic coatings, are well known for use as the lubricity agent for facilitating donning of the glove. An additional purpose is to provide protection to the user's skin. To that end, a colloidal oatmeal extract may be coated onto the polymer coating, with the result that the polymer coating provides lubricity and the colloidal oatmeal extract provides skin healing and protection properties which are activated by perspiration from the user's skin. However, in the most preferred implementation of a powder-free glove, the colloidal oatmeal extract provides both the lubricity functionality and the skin protectant functionality, whereby the polymer coating can be omitted.

Additional plant starch components can be combined with the colloidal oatmeal extract in order to provide other benefits such as cost reduction, additional starch proteins, film forming benefits, and the like.

Where the skin benefits which attend colloidal oatmeal are not necessary to the functionality required of a particular glove, the powder free extract can be made from any of a wide variety of powdered grains, either taken alone or in combination, whether whole grain or the starch extract of such grain. Thus there can be mentioned, for example and without limitation, rice and rice starch, corn and corn starch, amaranth and amaranth starch, oat and oat starch, and the like. For example, rice starch can be substituted in whole or in part for colloidal oatmeal, thus to form a lubricity coating. Rice starch can be combined with colloidal oatmeal to form a lubricity coating which provides the additional skin protectant functionality.

One version of the powder-free glove disclosed herein includes a coating that includes colloidal oatmeal that has been processed to extract many of the beneficial qualities of colloidal oatmeal while eliminating nearly all of the powder in the coating. As a result, the benefits of colloidal oatmeal may be enjoyed in a powder-free coating on a glove or other elastomeric article. Colloidal oatmeal USP is recognized as a product which is capable of healing and protecting the skin. Colloidal oatmeal USP is classified by the United States Food and Drug Administration (FDA) as an over-the-counter drug due to its ability to heal and protect the skin. Other coatings for gloves are currently not classified by the FDA as over-the-counter drugs.

The beneficial components of colloidal oatmeal are:

1) Polysaccharides—Colloidal oatmeal has a high polysaccharide content and forms a gelatinous hydrocolloid in water, which leaves a protective film on the skin that physically retards water loss. Additionally, this film helps to repair and maintain the epidermal barrier.

2) Oat lipids—These agents add to oatmeal's moisturizing, barrier-enhancing properties.

3) Oat proteins—These proteins have the ability to buffer both acids and bases that aid in barrier maintenance and repair.

4) Saponins—These ingredients within oatmeal help to solubilize dirt, oil and sebaceous secretions.

Figure 6:
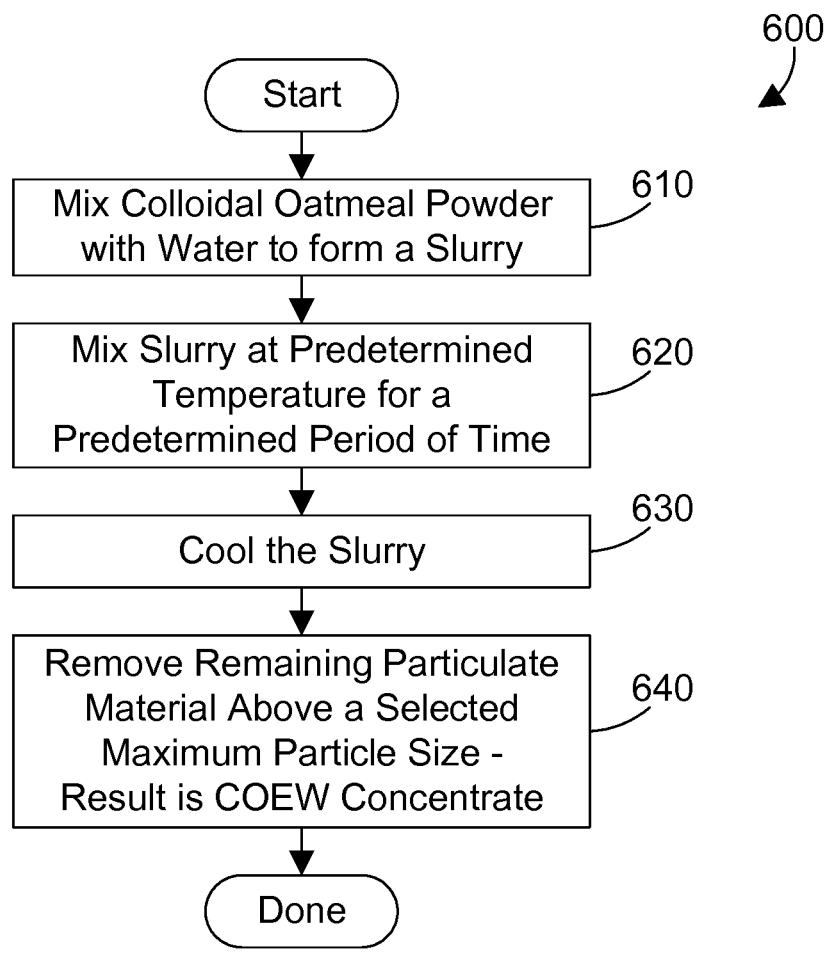
FIG. 6 is a flow diagram of a method for manufacturing colloidal oatmeal enhanced water (COEW)

Referring to FIG. 6, a method 600 for making colloidal oatmeal enhanced water (COEW) starts by mixing colloidal oatmeal powder with water to form a slurry (step 610). The slurry is then mixed at a predetermined temperature for a predetermined period of time (step 620). The mixing in step 620 allows many of the beneficial properties of colloidal oatmeal to be extracted from the colloidal oatmeal into the water in a powder-free form. The slurry is then cooled (step 630). The remaining particulate material above a selected maximum particle size is then removed, resulting in colloidal oatmeal enhanced water (COEW) concentrate (step 640). To produce what is defined as a powder-free glove, the FDA states there needs to be less than 2 milligrams of total particulate on the finished glove per the ASTM test D6124. The COEW that results from method 600 is a liquid coating that may be applied to gloves and then dried to provide a powder-free coating which provides many of the beneficial properties of colloidal oatmeal in a powder-free form. Note that the term "powder-free" as used in the specification and claims herein does not mean the complete absence of powder in the coating, but instead denotes a concentration of powder in the coating that is sufficiently small to meet government and/or industry standards for a powder-free glove.

The predetermined particle size in the slurry that is removed in step 640 of FIG. 6 may vary within the scope of the disclosure and claims herein. The predetermined particle size is 2.0 micron, is more preferably 1.5 micron, and is most preferably 1.0 micron. Thus, step 640 in FIG. 6 removes most of the particles above a predetermined particles size, however that predetermined particle size may be defined. Note, however, that step 640 may not remove every single particle above the predetermined size. The resulting COEW may also include a concentration of particles above the predetermined size that is less than a predetermined threshold. This allows some very small amount of particles above the predetermined size to be present in the COEW, so long as the amount still results in a powder-free glove. For example, if the predetermined threshold were selected to be one percent, this means the COEW could have less than one percent particles above the predetermined size. The predetermined threshold could be specified in any suitable unit of measure, including without limitation percent, milligrams, a ratio, etc.

In the past, colloidal oatmeal has been used as a dry donning agent on gloves. The Ostar glove, which has been commercially available since 1996, used a dry powder derived from colloidal oatmeal powder as a coating. Colloidal oatmeal is a well-known skin conditioning substance, skin moisturizing substance, skin softening substance, skin nourishing substance, skin emollient substance, and skin anti-inflammatory substance. Colloidal oatmeal is a powdered product which, if put onto a glove in an amount which would allow it to be effective in protecting and healing skin, would cause the glove to exceed the powder limits for a powder-free glove.

A detailed process for making COEW concentrate is now presented as one specific implementation of method 600 in FIG. 6. The colloidal oatmeal USP must go through a process where the beneficial components of the colloidal oatmeal are extracted from the grain particle into a water carrier. The extraction process is most efficient if the colloidal oatmeal powder, which is typically 4 to 30 microns in size. Note that the colloidal oatmeal powder could be further reduced in size by additional milling or filtering within the scope of the disclosure and claims herein. One part colloidal oatmeal is mixed with nine parts ionized water, by weight, to form a slurry. The water temperature is preferably between 35 to 49 degrees Celsius, more preferably between 40 to 49 degrees Celsius, and is most preferably between 45 to 49 degrees Celsius. A temperature in excess of 49 degrees Celsius will cause the colloidal oatmeal slurry to gel, and causes some or all of the active ingredients in the colloidal oatmeal to be denatured. For this reason, the temperature is preferably kept less than 50 degrees Celsius. The mixture is preferably mixed vigorously at as high a speed as commercially viable. The mixing equipment is preferably able to cut and shear the mixture as it mixes. The mixing time is at least 15 minutes, preferably at least 30 minutes, and most preferably at least 60 minutes. Temperature should be maintained between 45 to 49 Celsius as the slurry is mixed. Once the mixing is complete, the remaining particulate that is above a predetermined particle size is removed from the slurry. This may be done in any suitable way. For example, one way to remove the undesired particulate uses a decanter type centrifuge. Another way to remove the undesired particulate is by allowing the remaining oat particulate material to settle to the bottom and separating the liquid from the settled particles, either by extracting the resulting COEW concentrate from the top or by forcing the particles out the bottom until there is only liquid left. Yet another way to remove the undesired particulate is by filtering the mixture, thereby producing COEW concentrate. The resulting COEW concentrate contains the beneficial properties of Colloidal Oatmeal USP, as described in DEPARTMENT OF HEALTH AND HUMAN SERVICES, Food and Drug Administration, 21 CFR Parts 310, 347, and 352, Docket Nos. 78N-0021 and 78N-021P, RIN 0910-AA01, Skin Protectant Drug Products for Over-the-Counter Human Use. As a result, the COEW concentrate may be applied to a glove, then dried, resulting in a glove that provides beneficial concentrations of ingredients of colloidal oatmeal in a form that may be used to produce a powder-free glove.

The COEW is preferably applied to an elastomeric article in a concentration of 100%, but the viscosity of COEW without further modification would not provide optimal results in a glove manufacturing process. Without further modification the COEW does not equally disperse nor does it adhere well to the surface of the glove. To overcome this problem, a cellulose based thickening agent that does not interfere with the manufacturing process is preferably added to the COEW slurry. The preferred thickening agent is carboxymethylcellulose, which is added at a concentration of 0.1% to 0.5% by weight. Carboxymethylcellulose is available as Gabrosa DT 732 manufactured by Akzo Nobel Chemicals, available from the distributor Chung Chemicals SDN BHD A-42-3 Sri Desa Entrepreneurs Park, Jalan 1/116B, Off Jalan Kuchai Lama 58200, Telephone: 603 7987 7611.

COEW is highly susceptible to bacteria growth when in the liquid form. Once the COEW is applied to a glove and dried, there is typically no issue with bacterial growth in the dried COEW coating as long as the gloves are stored in a cool, dry place. If the COEW concentrate in liquid form needs to be stored or remains unused over a period of time, a suitable preservative (such as a bactericide) may be used to keep the bacteria in the COEW concentrate to an acceptable level. One suitable bactericide is commercially known as Biostat G7, which is commercially manufactured and marketed by Chempro Technology, Lot #27, Jalan Lada Hitam 16/12, Kawasan MIEL, Phase VII, 40000 Shah Alam Selangor, Malaysia. Other preservatives such as diazolidinyl urea, iodopropynyl butylcarbamate and propylene glycol could be used. The specific proportions needed depend on the time of storing the COEW, temperature, etc. One suitable mix of preservatives is 0.07% chloracedamide and 0.03% sodium benzoate. One skilled in the art will realize that the specific types and amounts of preservatives may vary depending upon the particular application.

Given the above method of making COEW concentrate, the COEW can be made in a variety of concentrations, with resulting protein contents as follows.

| Ex. No. | g. oatmeal/ 100 ml H2O | Mix Time | Mix Temp | Heating Time | Centrifuge RPM | Centrifuge Time | Protein ug/g |
|---|---|---|---|---|---|---|---|
| 1 | .0115 | 1 min | 44 C. | 45 min | 2000 | 20 min | 2.39 |
| 2 | .313 | 1 min | 44 C. | 45 min | 2000 | 20 min | 2.04 |
| 3 | 10 | 1 min | 44 C. | 45 min | 2000 | 20 min | 3.53 |
| 4 | 15 | 1 min | 44 C. | 45 min | 2000 | 20 min | 3.26 |
| 5 | 20 | 1 min | 44 C. | 45 min | 2000 | 30 min | 3.53 |
| 6 | 25 | 1 min | 44 C. | 45 min | 2000 | 30 min | 3.95 |
| 7 | 30 | 1 min | 44 C. | 45 min | 2000 | 30 min | 4.47 |

Examples 1-4 remained turbid at 20 minutes centrifuge time. Increasing the centrifuge time in Examples 5-7 produced a clear supernatant liquid. While a centrifuge was used in Examples 1-7, simply letting the particulate matter settle out of the slurry is believed to provide an equally acceptable process.

Once the supernatant liquid (COEW concentrate) is obtained, the liquid can be used without dilution, or can be diluted as desired. Using the 10 gram/100 ml water addition rate for making the COEW concentrate in Example 3, the inventors herein have found a 5/1 dilution rate, namely 4 parts water to 1 part COEW concentrate, to provide a dry coating which consists of 10 micrograms of protein per gram of dried COEW on the glove, using the ASTM 5712 Standard Test Method for Protein. A 5/2 dilution rate provided a coating weight of 20 micrograms (ug) of protein per gram of dried COEW on the glove.

Particle size in the resultant COEW is preferably relatively small. In the above Examples 1-7, particle size was 2 microns or less in the supernatant COEW concentrate.

Figure 7:
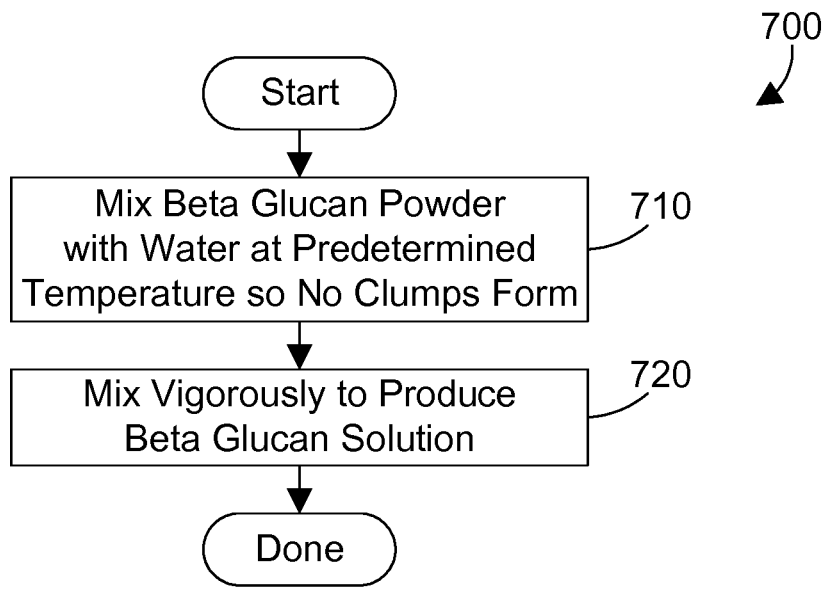
FIG. 7 is a flow diagram of a method for manufacturing beta glucan solution (BGS)

Another liquid may be used as a coating for elastomeric articles such as gloves. Beta glucan is a derivative that is available from many natural sources, including oats, wheat barley, baker's yeast, and mushrooms. The most preferred form of beta glucan is oat beta glucan that is available as Nurture® Beta-Glucan 70 PC which is available from Nurtured, Inc., 5840 Expressway, Missoula, Mont. 59808, 888-395-3300. This form of beta glucan is preferred because it is completely water-soluble. Referring to FIG. 7, a method 700 for producing a beta glucan solution begins by mixing beta glucan powder with water at a predetermined temperature in a manner that clumps do not form (step 710). The resulting mixture is mixed vigorously to produce beta glucan solution (BGS) (step 720). The BGS may then be applied to gloves or other elastomeric articles, either full-strength or in a diluted form. One of the benefits of using this particular form of beta glucan instead of colloidal oatmeal is that beta glucan is water-soluble. As a result, all of the beta glucan goes into solution, which eliminates the need to remove particulate material (as is necessary in step 640 in FIG. 6 during the production of COEW).

Beta glucan is an excellent ingredient for glove coatings because beta glucan has been shown to stimulate collagen production, revitalize and rejuvenate skin, reduce stinging in alpha-hydroxy acid formulations, is an anti-inflammatory, and provides cellular protection against ultraviolet (UV) radiation. Note that not all beta glucan is completely water-soluble. Some products are only partially water-soluble, and the water-solubility may be specified as percentage. Beta glucan that is not completely water-soluble may also be used within the scope of the disclosure and claims herein. If the beta glucan is not completely water-soluble, the resulting mixture will be part-solution (for the part that is water-soluble) and part suspension (for the part that is not water-soluble). The term "beta glucan solution" and "BGS" as used in the disclosure and claims herein expressly includes any liquid that contains beta glucan that is either partly or completely water-soluble, regardless of whether or not the liquid contains particles in suspension as well.

The BGS resulting from performing method 600 in FIG. 6 may be applied to gloves full-strength, but is preferably diluted with water. The dilution may provide for a concentration of BGS of less than 50%, more preferably less than 20%, and most preferably from 1-5%. Note that the concentration of BGS may be any suitable concentration from less than 1% up to and including 100%, and will depend on the desired feel of the glove, where higher concentrations of BGS provide a more discernible feel on the hands of the user.

A detailed process for making BGS is now presented as one specific implementation of method 700 in FIG. 7. For this example, we assume oat beta glucan is used. Oat beta glucan is refined beta-glucan, defatted, un-denatured oat protein in the form of fine micro porous particles. The INCI (International Nomenclature Cosmetic Ingredient) name for oat beta glucan is simple "beta glucan". Glucans are polysaccharides made up of chains of glucose molecules. The term "beta" refers to the steric position of the glucose hydroxyl group involved in the chain formation. The terms beta-1,3- and beta-1,6-glucans are often used, with the numbers referring to the positions on the glucose molecules that link them together. Beta-glucans are considered to be water-soluble fiber and are non-digestible, due to the absence in the human body of an enzyme capable of hydrolyzing the beta-glucosidic linkage. Some of the benefits of oat beta glucan are:

1) Cellular protection against UV
2) Stimulates collagen production
3) Anti-inflammatory
4) Moisturization via humectancy Oat beta glucan needs to be placed into a water carrier in order to be used in a glove manufacturing process. The steps required to mix oat beta glucan in water are disclosed below.

A maximum of up to 2% oat beta glucan can be mixed with 98% ionized water, by weight. Concentrations of more than 2% will cause the Beta Glucan to not be completely soluble and it will settle out rather than remain in solution. When mixing oat beta glucan and the water, the temperature of the water is preferably 80 to 90 degrees Celsius. The water is preferably circulated in a mixing unit which causes a circular vortex in the water. The beta glucan powder is preferably added at the center of the vortex very gradually as not to allow any of the powder to clump. If the powder clumps it will not properly go into solution, and some of the powder will remain in powder form in suspension in the water. The mixture of water and oat beta glucan powder is preferably mixed vigorously at as high a speed as commercially feasible and viable. The resulting product is beta glucan solution (BGS).

BGS is highly susceptible to bacteria growth. Once the BGS is applied to a glove and dried, there is typically no issue with bacterial growth in the dried BGS coating as long as the gloves are stored in a cool, dry place. If the BGS in liquid form needs to be stored or remains unused over a period of time, a suitable preservative (such as a bactericide) may be used to keep the bacteria in the BGS to an acceptable level. The same preservatives may be used with BGS that are listed above for COEW, namely Biostat G7, diazolidinyl urea, iodopropynyl butylcarbamate and propylene glycol. The specific proportions needed depend on the time of storing the BGS, temperature, etc. One suitable mix of preservatives is 0.07% chloracedamide and 0.03% sodium benzoate. One skilled in the art will realize that the specific types and amounts of preservatives may vary depending upon the particular application.

In one specific implementation, the COEW and BGS are mixed. When the two are mixed, the resulting mixture is referred to herein as "Polycoat" to represent that a dried coating of the liquid includes multiple beneficial ingredients. Production trials using various combinations of COEW and BGS in the Polycoat show that the levels of BGS that can be used in the manufacturing process range from as low as 0.1% to up to 50% of the 2% concentrated solution. Various mixtures of the COEW and the BGS can then be used in the glove manufacturing process. The mixture percentages used would be determined based on the desired outcome of the glove product. The range of mixtures of the COEW and the BGS could vary from 1% to 100% of the COEW and 0.1% to 50% of the BGS.

Figure 8:
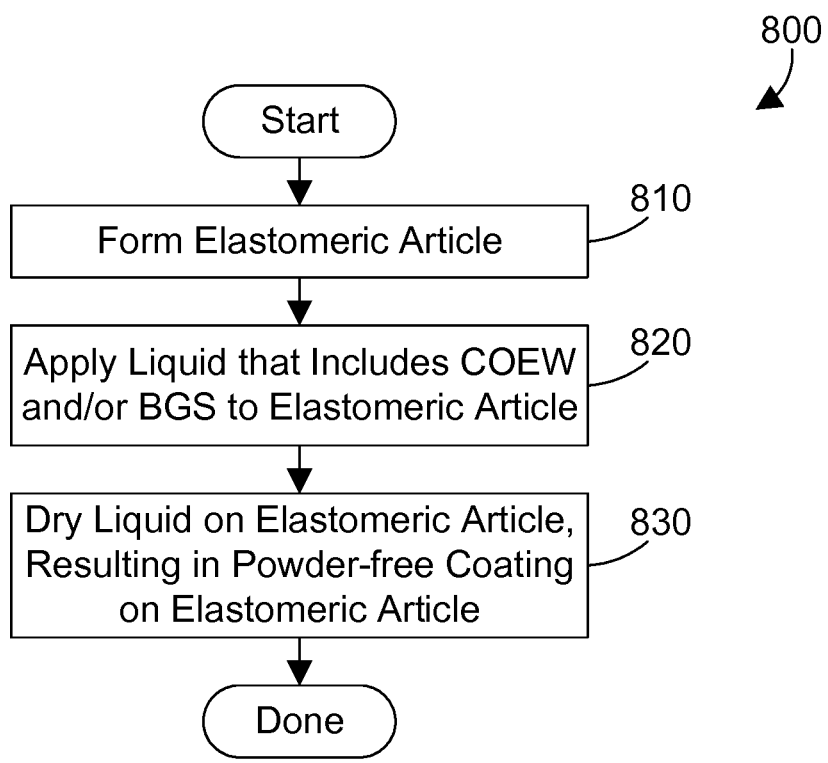
FIG. 8 is a flow diagram of a method for manufacturing an elastomeric article that includes a powder-free coating derived from COEW, BGS or Polycoat.

Referring to FIG. 8, a method 800 for manufacturing an elastomeric article begins by forming the elastomeric article (step 810). The article may be formed by any suitable method, whether currently known or developed in the future. A liquid that includes COEW and/or BGS is then applied to the elastomeric article (step 820). There are many different ways to apply the liquid to the elastomeric article in step 820, including dipping, spraying, tumbling and spraying, etc. The liquid is then dried on the article, resulting in a powder-free coating on the elastomeric article (step 830). If the article being manufactured is a glove, one suitable way to dry the liquid is to pass the gloves through a series of ovens designed to dry and cure the glove. This drying process causes the dried coating to tightly bond with the glove surface so that it remains in tact until the glove is donned by the user.

The size of particulates in the liquid coatings that include COEW, BGS, or both (Polycoat) is less than a predetermined maximum particle size. As a result, a coating that uses these materials results in a fine powder that aids in donning the glove, but the powder is not detectable using the standard ASTM D6124 test, resulting in a glove that may be easily donned due to the fine powder coating but still qualifies as a powder-free glove under industry standards.

In the manufacturing of gloves, even distribution of the liquid (e.g., COEW, BGS or Polycoat) on the glove surface maximizes therapeutic treatment of the hand and minimizes contact between the skin and the glove's composite material. Stationary drying is not preferred because the liquid tends to flow in the direction of the force of gravity. In the preferred manufacturing method the glove is spayed with the liquid coating. In another method the glove can also be dipped into a tank containing the liquid coating. Whether sprayed or dipped, when the glove comes away from the particular application process the porcelain glove mold rotates the glove as it passes through the drying ovens to make the liquid distribute evenly on the glove surface and to form a uniform coating. This would be for an online manufacturing process but in a less technologically advanced manufacturing facility where an on line method of manufacturing is not possible, the gloves can be taken to an offline tumbling dryer and the liquid can be sprayed on in the tumbler during the drying process.

In the preferred manufacturing method, once the gloves have passed through the drying ovens the gloves are then stripped from the porcelain glove molds using a process called air stripping. If air stripping is not a feature of the manufacturing line the gloves can also be removed manually from the porcelain glove mold former. In either stripping method the gloves are inverted so that the surface with the dried coating is now on the inside of the glove or the side the glove the user would primarily come in contact with.

The preferred method for the most cost efficient production of the coated powder-free glove requires a fully automated production line using industry standard porcelain glove mold formers where the various described processes are accomplished. This more advanced automated method is preferred and best suited for producing the gloves in substantially larger quantities and at a lower cost.

The preferred method of manufacturing is fully automated within the production line, meaning that no (or minimal) offline steps are required. The gloves are formed on porcelain glove molds in a similar fashion to standard technology, but the primary difference being that the mold release agent, which is the substance the manufacture places between the porcelain glove mold and the substrate material, is a powder free, polymer material. In less automated facilities where less current technology is available a powdered substance of calcium carbonate is used as the mold release agent. Once a powdered mold release agent is used there is no way to remove the unwanted mold release agent powder without removing the glove from the mold and taking it to some offline type of washing process. Typically this process requires that the gloves be put into offline washing units where they are once again taken through a chlorination process. This causes unnecessary steps in the manufacturing process and increases the product cost which must be passed to the glove consumer. The large purchasing groups which provide gloves to the larger users of gloves like hospitals and nursing homes are extremely price sensitive. If the preferred method of manufacturing, a fully automated process is not used, very few of these types of glove consumers would be able to take advantage of a glove containing a skin protecting and healing substance.

In this method the gloves which are formed on the porcelain glove mold currently are in an inside out position. So the surface which currently is the exterior surface when stripped from the porcelain glove mold and turned inside out will become the inside, or user side/surface of the glove which will come in contact with the user and deliver the dose of beneficial ingredients in the dry coating to the users skin.

To achieve a surface on the inside or users side of the glove, a chlorination washing process is the common process for making this surface slippery enough to allow the user to easily slip their hand into the glove. There are other layers/surfaces that can be added to the gloves surface alone or in conjunction with chlorination on the user side of the glove such as acrylic polymers or silicone or polyurethane to cause the glove to be more easily donned.

Following the application of an adequate donning surface, such as a polymer layer, the liquid (e.g., rice starch liquid, COEW, BGS or Polycoat) is applied to the gloves while the gloves are still on the molds, either by dipping or by spraying. If spraying is used, it should be a sufficient dosage so as to leave a desired amount of solution on the gloves' inside out surfaces. Dipping and spraying are very different types of processes which will require unique viscosities for each method. Viscosity required will depend upon many factors including the type of layers/surfaces that have been added to the gloves surface alone or in conjunction with chlorination on the user side of the glove such as acrylic polymers or silicone or polyurethane to cause the glove to be easily donned, and other manufacturing line considerations like the speed of the line.

Following this application of the liquid the gloves go through a drying process. In this preferred method, as the glove continues to travel down the manufacturing line, circulating heated air will be moved around the molds which hold the partially vulcanized latex glove. As the glove continues to vulcanize with the coating adhered to the surface the rubber partially bonds with the coating causing a tighter and longer lasting bond to form. From line to line temperatures will vary based on the length available for drying purposes. Typical heating ranges from 110 and up to 130 degrees Celsius.

The application of Polycoat to gloves needs to occur following steps in the manufacturing process which causes the glove to be clean from contaminants and the steps which create the layers/surfaces that can be added to the gloves surface alone or in conjunction with chlorination on the user side of the glove such as acrylic polymers or silicone or polyurethane to cause the glove to be more easily donned.

Contaminants are primarily the powders and airborne particulate found in a factory environment and the water soluble latex proteins and other chemical residues like accelerators used to help vulcanize the glove rubber. In the preferred embodiment, due to cost considerations, an online manufacturing method is preferred. Many glove manufacturers, due to a lack of technology and equipment, must take the gloves off the line to washers, tumblers and drying equipment to add other desired types of surface treatments, but in this preferred method the entire process takes place online and thus there are significant cost savings. The viscosity and concentration of the liquid coating is specifically designed to allow for an online application. In the preferred manufacturing method, the online application of liquid coating is also unique in that it is sprayed on versus dipped into a tank as in the majority of manufacturing operations. Although a dipping tank scenario would be the easiest way to apply the coating, a dipping tank will cause the dangerous water soluble proteins found in the gloves to be leached out into the liquid as each glove passes through the dip tank. Very rapidly these allergenic water soluble proteins will build up in the tank and begin finding their way back to the surface of the other gloves. Dipping is only an acceptable application method if the manufacturer is willing to monitor the protein buildup in the tank and change to a fresh tank of the liquid as necessary. But once again this method will cause unnecessary cost to be added to the glove. In this preferred online method the gloves go through virtually every step of the manufacturing process except the final drying ovens. Just prior to the final drying ovens a spray station is incorporated into the manufacturing line to spray the liquid onto the glove. In an online application of the coating the spray station sprays the desired amount of liquid onto the glove and the glove then proceeds to the drying ovens where the water carrier is evaporated from the liquid, resulting in a dry coating on the surface of the glove. In the final removal of the glove from the porcelain glove mold the glove is stripped and turned inside out which puts the dried coating on to the inside or donning surface of the glove.

Another method which can be used is online dipping. The steps are the same as those described in the online spray method, except the glove is dipped in a tank of liquid instead of sprayed with the liquid. The cost saving aspects of being able to manufacture larger quantities at lower prices is somewhat maintained, but there is a problem with a build up of allergenic latex protein which will then be transferred back to other gloves if the tank is not regularly monitored for the water soluble protein and changed as necessary.

If this online method is not available due to a lack of technology and equipment, the gloves can be coated using an offline manufacturing method. Here the liquid is applied to the gloves by spraying a batch of clean loose gloves that are arranged inside out. But bear in mind that turning the gloves is a manual process which creates additional expense. The gloves are tumbled so that hopefully the surfaces of every glove will have a better chance of being exposed to liquid as it is sprayed in the tumbler. This step of tumbling of the gloves continues to occur even after the spraying of the liquid has already stopped. This keeps the gloves from sticking together and gives the best chance that the liquid coating is uniformly applied. The spraying and tumbling are then preferably repeated for the desired number of times. After the last application the liquid to the gloves, the gloves are completely dried by tumbling with heating until the gloves are dry. The number of times this process must be done in an offline method needs to be sufficient, given the particular dryer and spray nozzle configuration, to leave at least a desired minimum amount, and/or no more than a desired maximum amount, of coating on substantially every glove. In this more costly and less desirable method the gloves need to be turned one time prior to their being coated with the liquid and then once the coating has been applied and dried they must be manually turned again.

Preferably, the spraying and drying steps can all be performed within a commercial heat tumble dryer, for example, as follows. After a water bath at the end of the chlorination process the gloves are removed from the water bath and dumped into the heat tumble dryer. The dryer then starts tumbling the gloves. Preferably, the tumbling is accompanied by heating of the gloves with hot air and continues until the gloves are dry or mostly dry. Then, a spray nozzle configured to spray the liquid as a fine mist starts spraying the liquid onto the gloves in the dryer. During the spraying, the tumbling and heating continues as necessary. The spraying and tumbling may be repeated for several iterations. After the last iteration of spraying, the gloves are dried, preferably by tumbling with heating until the gloves are dry. The number of cycles and length of the cycle durations and the amount of liquid to use should be chosen to be sufficient, given the particular dryer and spray nozzle configuration, to leave at least a desired minimum thickness, and/or no more than a desired maximum thickness, of dried coating on substantially every glove.

The amount of liquid required in an offline application depends upon the size of the batch, the method for applying the liquid and the thickness of the desired coating. For example, for a batch of about 3000 gloves, two kilograms of rice starch liquid, COEW, BGS, or Polycoat may be sprayed in about 4 or 5 spray iterations, with the spray iterations spaced about 2 to 5 minutes apart, and with each spray iteration having a spray duration of about 30 to 90 seconds in a tumbling dryer. Each spray cycle is preferably followed by a tumbling cycle. The final iteration of tumbling is of sufficient duration to dry the gloves and especially should include heating. For example, the final iteration of tumbling may be chosen so that the total duration of tumbling and heating gloves where the liquid is applied for all the steps is about 35 to 40 minutes.

The overall objective is to coat the glove with a water extract of the selected starch composition, whether single grain or multiple grain, or perhaps non-grain starch, optionally including the colloidal oatmeal and/or beta glucan, for their skin protectant properties. The liquid is dried on the glove to leave a film-like coating which can have embedded therein smaller particles of the beneficial material where the slurry does not exceed the gelatinization temperature of a respective starchy component.

Where the starch/grain composition of the so-developed liquid does not contain colloidal oatmeal, or contains only a small fraction of colloidal oatmeal, then the nomenclature may change to something like Starch Extract Water or Grain Extract Water, or some other such nomenclature. However, in the interest of consistency herein, unless otherwise specifically indicated, all such compositions are herein referred to generically as COEW.

As appreciated by those skilled in the art, the rice starch powder, with or without colloidal oatmeal, with or without additive(s) 20, and with or without the alternative dry powdered plant materials described previously herein; or in the alternative COEW, BGS or Polycoat; can be used to apply a coating to any flexible elastomeric article, not necessarily just glove 10 shown in FIG. 1, having at least one elastomer layer and having a wearer-contacting surface and a distal surface disposed distal the wearer-contacting surface, using the methods disclosed herein. An exemplary flexible elastomeric article to which the dry powdered rice starch, with or without the additives, or COEW and/or BGS, may be applied, includes a condom.

One skilled in the art will appreciate that many variations are possible within the scope of the claims. Thus, while the disclosure is particularly shown and described above, it will be understood by those skilled in the art that these and other changes in form and details may be made therein without departing from the spirit and scope of the claims.

What is claimed is:

1. A method for manufacturing a liquid that includes beta glucan, the method comprising the steps of:
    Mixing a predetermined quantity of beta glucan powder with a predetermined quantity of water in a manner that minimizes likelihood of clump formation in the resultant mixture, and
    Mixing the mixture to produce a beta glucan solution that has a concentration of particles having a size greater than a selected maximum particle size that is less than a predetermined threshold.

2. An elastomeric article coated with a dried form of the liquid manufactured in claim 1.

3. The elastomeric article in claim 1 wherein the elastomeric article comprises a glove.

4. The method of claim 1 where the beta glucan comprises oat beta glucan.

5. The method of claim 1 wherein the concentration of the beta glucan in the beta glucan solution is from 1% to 50% by weight.

6. The method of claim 1 further comprising the steps of:
    mixing powdered colloidal oatmeal with particles smaller than two microns with water at a temperature less than 50 degrees C. to form a slurry;
    holding the slurry at a temperature of 30 to 50 degrees C. for at least 15 minutes;
    cooling the slurry;
    while maintaining the slurry in the cooled condition, removing remaining particulate material above a selected maximum particle size, thereby producing a liquid having a concentration of particles having a size greater than the selected maximum particle size that is less than a predetermined threshold; and
    mixing the liquid with the beta glucan solution.

7. The method of claim 6 wherein the step of removing remaining particulate material above the selected maximum particle size is performed using a centrifuge.

8. The method of claim 6 wherein the step of removing remaining particulate material above the selected maximum particle size is performed by allowing the cooled slurry to sit for a predetermined time to allow particles to settle to the bottom, and removing the liquid from the top of the slurry.

9. The method of claim 6 wherein the step of removing remaining particulate material above the selected maximum particle size is performed using a filter.

10. A method for manufacturing an elastomeric article having a flexible body having an inner cavity, the inner cavity defining an inner surface of the body, an outer surface being defined outwardly of the body, the method comprising the steps of:

(A) forming the elastomeric article;

(B) applying a liquid comprising beta glucan to the elastomeric article, the liquid having a concentration of particles having a size greater than a selected maximum particle size that is less than a predetermined threshold; and (C) drying the liquid to form a substantially dry coating on the elastomeric article that provides less than a specified amount of particulate on the elastomeric article, resulting in a substantially powder-free elastomeric article.

11. The method of claim 10 wherein the liquid further comprises colloidal oatmeal with particles smaller than two microns.

12. The method of claim 10 wherein the beta glucan comprises oat beta glucan.

13. The method of claim 10 wherein the elastomeric article comprises a glove.

14. The method of claim 10 wherein the specified amount of particulate is 2 milligrams.

15. The method of claim 10 wherein the selected maximum particle size is 2 microns.

* * * * *